United States Patent [19]
Laskey et al.

[11] Patent Number: 6,107,042
[45] Date of Patent: Aug. 22, 2000

[54] CELL-FREE SYSTEM FOR INITIATION OF DNA REPLICATION

[75] Inventors: Ronald Alfred Laskey; Torsten Krude; Mark Richard Jackman; Jonathan Noe Joseph Pines, all of Cambridge, United Kingdom

[73] Assignee: Cancer Research Campaign Technology Limited, London, United Kingdom

[21] Appl. No.: 09/214,070

[22] PCT Filed: Jun. 26, 1997

[86] PCT No.: PCT/GB97/01751

§ 371 Date: Jan. 25, 1999

§ 102(e) Date: Jan. 25, 1999

[87] PCT Pub. No.: WO97/49797

PCT Pub. Date: Dec. 31, 1997

[30] Foreign Application Priority Data

Jun. 26, 1996 [GB] United Kingdom .................. 9613418

[51] Int. Cl.$^7$ .............................. C12Q 1/68; C12P 19/34
[52] U.S. Cl. .................................. 435/6; 435/15; 435/91.1
[58] Field of Search ................................. 435/6, 91.1, 15

[56] References Cited

U.S. PATENT DOCUMENTS 5,635,349  6/1997  LaMarco et al. ........................... 435/6
5,645,999  7/1997  Roberts et al. ........................ 435/7.4

FOREIGN PATENT DOCUMENTS

WO 93/06123  4/1993  WIPO .

OTHER PUBLICATIONS

Heintz et al., Mol. Cell. Biol. 8(5), 1923–1931 (1988).
Leno et al., Cell 69, 151–158 (1992).
Heichmann, K.A. and Roberts, J.R.: "Rules to replicate by", Cell, vol. 79, 1994, pp. 557–562.
Nurse, P., "Ordering S phase and M phase in the cell cycle", Cell, vol. 79, 1994, pp. 547–550.
Krude et al, "Cyclin/Cdk–Dependent Initiation of DNA Replication in a Human Cell–Free System", Cell 88:109–119 (1997).
Otaegui et al, "Transfer of Nuclei From 8–Cell State Mouse Embryos Following Use of Nocodazole to Control the Cell Cycle", Molecular Reproduction And Development 39:147–152 (1994).
"Synchronisatino of cells in the G1–phase of the cell cycle—with maximum possible synchronisation of clel culture in the G1–phase irrespective of the type of the cell culture", Database WPI Abstgract No. 98–191873.
Williams et al, "A human protein related to yeast Cdc6p", Proc. Natl. Acad. Sci. USA 94:142–147 (1997).
Wilmut et al, "Viable offspring derived from fetal and adult mammalian cells", Nature 385:810–813 (1997).
Campbell et al, "Sheep cloned by nuclear transfer from a cultured cell line", Nature 380:64–66 (1996).
Coleman et al, "The Xenopus Cdc6 Protein Is Essential for the Initiation of a Single Round of DNA Replication in Cell–Free Extracts", Cell 87:53–63 (1996).
Stillman, "Cell Cycle Control of DNA Replication", Science 274:1659–1664 (1996).

Primary Examiner—Kenneth R. Horlick
Attorney, Agent, or Firm—Nixon & Vanderhye P.C.

[57] ABSTRACT

A cell-free system for initiating DNA replication under cell cycle control includes S phase cytosol or a fraction thereof in which are incubated G1 phase nuclei, which are co-incubated with S phase nuclei or a fraction thereof and/or cyclins A and/or E complexed to their cognate cyclin dependent kinase (Cdk2). The system may be used to assay for substances which modulate DNA synthesis or initiation thereof, and which have therapeutic potential in a number of contexts.

16 Claims, 6 Drawing Sheets

PHASE OF CYTOSOLIC EXTRACT

CELL-FREE SYSTEM FOR INITIATION OF DNA REPLICATION

The present invention relates to in vitro procedures for DNA replication, and more particularly provides a system for initiating semi-conservative DNA replication under somatic cell cycle control. It also relates to the use of such a system, for example in identifying agents that modulate DNA replication, in particular inhibit or stimulate it, thereby providing for example agents having utility based on therapeutic potential.

The initiation of DNA replication is a key step in the regulation of the cell division cycle. A plethora of intra- and extracellular signals is integrated during G1 phase of the cell cycle into a decision to withdraw from the division cycle, or to initiate S phase and hence to continue proliferation (Heichman and Roberts, 1994). Once S phase is initiated, control mechanisms ensure that all chromosomal DNA is replicated before chromosomes are segregated into the two daughter cells at mitosis (Nurse, 1994).

Cell fusion and nuclear transplantation experiments provided compelling evidence that quiescent cell nuclei are induced to initiate DNA replication when introduced into S phase cells (Graham et al., 1966; Harris et al., 1966; de Terra, 1967; Johnson and Harris, 1969). When synchronised cells were fused, S phase cells induced DNA replication only in G1 nuclei, but not in G2 nuclei (Harris et al., 1966; de Terra, 1967; Guttes and Guttes, 1968; Ord, 1969; Rao and Johnson, 1970). These results indicated that S phase cells contain dominant specific factors that trigger DNA replication and are evolutionarily conserved. Unreplicated G1 nuclei are the physiological substrates for the initiation of DNA replication, whilst re-replication in G2 nuclei is prevented until they have undergone mitosis (Romanowski and Madine, 1996).

Genetic evidence in the yeast *Saccharomyces cerevisiae* provided independent evidence for an inducer of S phase (Hartwell, 1974). The protein kinase CDC28 is a key regulator of the yeast cell division cycle (Nasmyth, 1993). It associates with different regulatory CLN and CLB cyclin subunits throughout the progression of the cell cycle to execute cell cycle-specific functions in a temporally regulated way. Association with G1 and S phase specific cyclins, followed by the postranslational activation of the catalytic subunit is essential for the onset of S phase in yeast (Nasmyth, 1993). In higher eukaryotes, the situation is more complex in that different catalytic cyclin-dependent kinase (Cdk) subunits associate with different cyclins at different times to regulate the progression of the cell cycle [reviewed in (Heichman and Roberts, 1994; Nurse, 1994; Sherr, 1994)]. Experiments with antibodies, antisense RNA constructs or ectopic expression of cyclin genes indicate a role of cyclins D, E and A in inducing the G1-to-S phase transition in somatic mammalian cells in vivo (Girard et al., 1991; Pagano et al., 1992; Zindy et al., 1992; Ohtsubo and Roberts, 1993; Resnitzky et al., 1994; Wimmel et al., 1994; Ohtsubo et al., 1995; Resnitzky and Reed, 1995).

Direct biochemical analysis of replication initiation in eukaryotic somatic cells has been impeded by the lack of an efficient mammalian cell-free DNA replication system to complement these cellular and genetic approaches. Existing cell-free DNA replication systems are inadequate for studying the initiation of chromosomal DNA replication for the following reasons:

First, viral cell-free systems such as that derived from Simian Virus 40 (SV40) and its somatic host cells depend on essential viral control elements in addition to mammalian cell extracts; namely cis-acting DNA viral sequences including the origin of bidirectional DNA replication and the trans-acting initiator protein T antigen (Li and Kelly, 1984; Challberg and Kelly, 1989; Stillman, 1989). Both control elements are virus-encoded and serve to overcome the cellular once-per-cell-cycle replication control allowing viral DNA runaway-replication to occur in the infected cell nucleus.

Second, a cell free system derived from activated eggs of the frog *Xenopus laevis* can replicate mammalian cell nuclei under early embryonic cell cycle control (Lohka and Masui, 1983; Blow and Laskey, 1986; Newport, 1987; Murray and Kirschner, 1989). These early embryonic cell cycles are unusual and differ significantly from the cell cycles of most somatic vertebrate cells. They last only 35 minutes, compared with approximately a day in somatic cells, and they consist of alternating S and M phases without intervening G1 and G2 phases. Therefore, the key regulatory steps of the somatic cycle, the G1-to-S and the G2-to-M transition are formally absent in the early embryonic cycles. Furthermore, the duration of S phase in the embryonic cycle (25 min) is more than an order of magnitude shorter than in the somatic cycle (approximately 8 h). Although these cell-free systems are valuable in identifying enzymatic and structural aspects of DNA replication, they are limited for studying the regulation of initiation under somatic cell cycle control.

The present invention is based on the development of a cell-free system from human cells that initiates DNA replication under cell cycle control. G1 but not G2 phase nuclei initiate replication when co-incubated with S phase nuclei in cytosolic extracts from S phase, but not from G1 or G2 phase cells. S phase nuclei in the incubation can be replaced by a salt extract or may be omitted, inducing initiation of semi-conservative DNA replication in G1 phase nuclei. This nuclear extract can in turn be replaced by cyclins A and E complexed to Cdk2, but not by Cdk2 alone or by human cyclin B1 complexed to Cdk2. (The inventors have used baculovirus-expressed recombinant human cyclins.) In S phase cytosol, cyclins A/Cdk2 and E/Cdk2 synergistically trigger initiation of DNA replication in G1 nuclei.

According to one aspect of the present invention, therefore, there is provided a cell-free system for initiating DNA replication under cell cycle control, including S phase cytosol, cytosolic factors or extract, i.e. a S phase cytolosic fraction, in which are co-incubated G1 phase nuclei, and S phase nuclei or a fraction thereof, and/or cyclins A and/or E (preferably both) complexed to their cognate cyclin dependent kinase (Cdk2) may also be included.

A suitable soluble extract of S phase nuclei is obtainable using an aqueous buffer, such as a NaCl solution, as disclosed in the experimental section below.

Also as discussed below, the inclusion of both cyclin A/cdk2 and cyclin E/cdk2, rather than one or the other complex, has a synergistic effect on the detectable level of DNA replication. If one or other or both of the cylcin/cdk complexes are included, the preferred concentration may be about 0.1–1 μg/ml.

Where applicable, instead of using a wild-type cyclin A and/or cyclin E and Cdk2, an amino acid sequence variant, mutant, derivative, allele or homologue may be employed which differs by one or more amino acid residues from the wild-type amino acid sequence, by one or more of addition, insertion, deletion and substitution of one or more amino acids. References to cyclin A and/or cylin E and cdk2 should be construed accordingly.

If S phase nuclei are included, a range of ratios in terms of numbers compared with numbers of G1 phase nuclei may be employed. While increasing the ratio of S:G1 phase nuclei increases the level of initiation of DNA replication, it also increases the level of background noise which at a certain point may begin to mask the signal. A number of ratios are illustrated in the experimental section and may be employed in accordance with different embodiments of the present invention. Thus, without limitation of the present invention, exemplary ratios include about 1:1, about 1:3 or more, about 1:1 or more, about 3:1 or more, about 5:1 or more, up to about 9:1 or more.

If S phase nuclei or a fraction thereof are included, this may be at around 1 to 2 hours after entry into S phase. Around 2 hours may be preferred.

G1 phase nuclei may be included at different times within G1 phase. It may be preferred for certain purposes to include the G1 nuclei in the late half of G1 phase, such as around two thirds through G1 phase, though for other purposes, e.g. in screening for substances able to stimulate initiation of DNA replication, it may be preferred to include the G1 phase nuclei in the early half of G1 phase, such as around one third through G1 phase. Of course, the absolute length of G1 phase varies from one cell or cell type to another.

The development of a human cell-free system that initiates semiconservative DNA replication under cell cycle control allows a wide range of experiments by fractionation, protein addition and selective immunodepletion of target proteins. This should allow further insights into the control of DNA replication and its coupling to the cell cycle in human cells. In addition, the system will allow a range of uses in deriving products of practical benefit, such as screening and identifying therapeutic agents which inhibit DNA replication, and which could thus be used as anti-cancer drugs, and also agents which stimulate DNA replication, which could be used for tissue repair therapeutics.

Accordingly, a further aspect of the present invention includes the use of a cell-free system for initiating DNA replication under cell cycle control in the screening or identifying of agents which modulate, e.g. inhibit or stimulate, DNA replication or synthesis, or initiation thereof.

Methods of obtaining agents able to modulate DNA replication or initiation thereof include methods wherein a suitable end-point is used in the presence and absence of a test substance. Detailed disclosure in this respect is included below. It is worth noting, however, that combinatorial library technology provides an efficient way of testing a potentially vast number of different substances for ability to modulate and activity. Such libraries and their use are known in the art, for all manner of natural products, small molecules and peptides, among others. The use of peptide libraries may be preferred in certain circumstances.

Appropriate agents may be obtained, designed and used for any of a variety of purposes.

Agents which inhibit DNA replication or synthesis or the initiation thereof may be used against cellular proliferative disorders, such as tumours/cancer, inflammation and psoriasis. They may be used for example in inducing apoptosis, in inhibiting cell replicationg, as anti-tumour or anti-inflammatory agents, and so on. Agents which stimulate DNA replication or synthesis or the initiation thereof may be used in any context where cellular stimulation is required or desirable, such as in promotion of angiogenesis, in healing of wounds, burns or tissue grafts. They may for example stimulate cell growth, cell regeneration, blood vessel formation, for instance in infarcted or compromised tissue, or in graft medication.

In one general aspect, the present invention provides an assay method for a substance with ability to modulate, e.g. inhibit or stimulate, DNA synthesis, the method including:

(a) treating a cell-free system as disclosed with a test substance; and (b) determining DNA synthesis.

A test compound which disrupts, reduces, interferes with or wholly or partially abolishes DNA synthesis or replication may thus be identified. Likewise, a test compound which stimulates, increases, potentiates or augments DNA synthesis or replication may thus be identified.

DNA synthesis may be determined by any suitable means which may conveniently involve labelling of a deoxynucleoside and determining incorporation of the label into DNA. Any suitable label may be employed, including radioactivity and fluorescence. Scintillation counting or FACS analysis may conveniently be employed. In principle the amount of DNA being synthesised may be measured, but this would not be compatible with high through-put screening of test substances.

Performance of an assay method according to the present invention may be followed by isolation and/or manufacture and/or use of a compound, substance or molecule which tests positive for ability to modulate DNA synthesis.

The amount of test substance or compound which may be added to an assay of the invention will normally be determined by trial and error depending upon the type of compound used. Typically, from about 1 pM to 1 mM or more concentrations of putative inhibitor compound may be used, for example from 0.01 nM to 100 $\mu$M, e.g. 0.1 to 50 $\mu$M, such as about 10 $\mu$M. Greater concentrations may be used when a peptide is the test substance. Even a molecule with weak binding may be a useful lead compound for further investigation and development.

Compounds which may be used may be natural or synthetic chemical compounds used in drug screening programmes. Extracts of prokaryotes and/or eukaryotes, such as plants, which contain several characterised or uncharacterised components may also be used.

Antibodies and binding fragments thereof directed to one or more components of DNA replication apparatus or other cellular component form a further class of putative inhibitor compounds. Candidate inhibitor antibodies may be characterised and their binding regions determined to provide single chain antibodies and fragments thereof which are responsible for disrupting the interaction.

Other candidate inhibitor compounds may be based on modelling the 3-dimensional structure of a polypeptide or peptide fragment and using rational drug design to provide potential inhibitor compounds with particular molecular shape, size and charge characteristics.

A compound found to have the ability to affect DNA replication has therapeutic and other potential in a number of contexts, as discussed. For therapeutic treatment such a compound may be used in combination with any other active substance, e.g. for anti-tumour therapy another anti-tumour compound or therapy, such as radiotherapy or chemotherapy. Thus, the assay of the invention, when conducted in vivo, need not measure the degree of modulation, e.g inhibition or stimulation, of DNA synthesis caused by the compound being tested. Instead the effect on cell viability, cell killing (e.g. in the presence and absence of radio- and/or chemotherapy), and so on, may be measured.

An agent identified using one or more primary screens as having ability to modulate DNA synthesis may be assessed further using one or more secondary screens. A secondary screen may involve testing for ability to enter a cell and be transported to the nucleus, and/or testing for ability to modulate cell replication.

Following identification of a substance or agent which modulates or affects DNA replication, the substance or agent may be investigated further. Furthermore, it may be manufactured and/or used in preparation, i.e. manufacture or formulation, of a composition such as a medicament, pharmaceutical composition or drug. These may be administered to individuals, e.g. for any of the purposes discussed elsewhere herein.

As noted, the agent may be peptidyl, e.g. a peptide which includes a sequence as recited above, or may be a functional analogue of such a peptide.

As used herein, the expression "functional analogue" relates to peptide variants or organic compounds having the same functional activity as a peptide in question. Examples of such analogues include chemical compounds which are modelled to resemble the three dimensional structure of a peptide or polypeptide domain, and in particular the arrangement of the key amino acid residues.

In a further aspect, the present invention provides the use of a substance identified or obtained using a cell-free system in accordance with the present invention in methods of designing or screening for mimetics of the substance.

Accordingly, the present invention provides a method of designing mimetics of a peptidyl substance able to modulate DNA replication identified or obtained using a cell-free system as disclosed, said method comprising:

(i) analysing the substance to determine the amino acid residues essential and important for the modulating activity to define a pharmacophore; and, (ii) modelling the pharmacophore to design and/or screen candidate mimetics having the modulating activity.

Suitable modelling techniques are known in the art. This includes the design of so-called "mimetics" which involves the study of the functional interactions fluorogenic oligonucleotide the molecules and the design of compounds which contain functional groups arranged in such a manner that they could reproduced those interactions.

The designing of mimetics to a known pharmaceutically active compound is a known approach to the development of pharmaceuticals based on a "lead" compound. This might be desirable where the active compound is difficult or expensive to synthesise or where it is unsuitable for a particular method of administration, e.g. peptides are not well suited as active agents for oral compositions as they tend to be quickly degraded by proteases in the alimentary canal. Mimetic design, synthesis and testing may be used to avoid randomly screening large number of molecules for a target property.

There are several steps commonly taken in the design of a mimetic from a compound having a given target property. Firstly, the particular parts of the compound that are critical and/or important in determining the target property are determined. In the case of a peptide, this can be done by systematically varying the amino acid residues in the peptide, e.g. by substituting each residue in turn. These parts or residues constituting the active region of the compound are known as its "pharmacophore".

Once the pharmacophore has been found, its structure is modelled to according its physical properties, e.g. stereochemistry, bonding, size and/or charge, using data from a range of sources, e.g. spectroscopic techniques, X-ray diffraction data and NMR. Computational analysis, similarity mapping (which models the charge and/or volume of a pharmacophore, rather than the bonding between atoms) and other techniques can be used in this modelling process.

In a variant of this approach, the three-dimensional structure of the ligand and its binding partner are modelled. This can be especially useful where the ligand and/or binding partner change conformation on binding, allowing the model to take account of this the design of the mimetic.

A template molecule is then selected onto which chemical groups which mimic the pharmacophore can be grafted. The template molecule and the chemical groups grafted on to it can conveniently be selected so that the mimetic is easy to synthesise, is likely to be pharmacologically acceptable, and does not degrade in vivo, while retaining the biological activity of the lead compound. The mimetic or mimetics found by this approach can then be screened to see whether they have the target property, or to what extent they exhibit it. Further optimisation or modification can then be carried out to arrive at one or more final mimetics for in vivo or clinical testing.

The mimetic or mimetics found by this approach can then be screened to see whether they have the target property, or to what extent they exhibit it. Further optimisation or modification can then be carried out to arrive at one or more final mimetics for in vivo or clinical testing.

Mimetics of this type together with their use in therapy form a further aspect of the invention.

Generally, such a substance, e.g. inhibitor or stimulator, according to the present invention is provided in an isolated and/or purified form, i.e. substantially pure. This may include being in a composition where it represents at least about 90% active ingredient, more preferably at least about 95%, more preferably at least about 98%. Such a composition may, however, include inert carrier materials or other pharmaceutically and physiologicaly acceptable excipients. As noted below, a composition according to the present invention may include in addition to an inhibitor compound as disclosed, one or more other molecules of therapeutic use, such as an anti-tumour agent.

The present invention extends in various aspects not only to a substance identified as a modulator of DNA replication, in accordance with what is disclosed herein, but also a pharmaceutical composition, medicament, drug or other composition comprising such a substance, a method comprising administration of such a composition to a patient, e.g. for a purpose discussed elsewhere herein, which may include preventative treatment, use of such a substance in manufacture of a composition for administration, e.g. for a purpose discussed elsewhere herein, and a method of making a pharmaceutical composition comprising admixing such a substance with a pharmaceutically acceptable excipient, vehicle or carrier, and optionally other ingredients.

A substance according to the present invention may be provided for use in a method of treatment of the human or animal body by therapy which affects DNA replication in cells, e.g. tumour cells. Other purposes of a method of treatment employing a substance in accordance with the present invention are dicussed elsewhere herein.

Thus the invention further provides a method of modulating DNA replication, e.g. for a purpose discussed elsewhere herein, which includes administering an agent which modulates DNA replication or synthesis, such a method being useful in treatment where such modulation is desirable.

The invention further provides a method of treatment which includes administering to a patient an agent which modulates DNA replication or synthesis. Exemplary purposes of such treatment are discussed elsewhere herein.

Whether it is a polypeptide, antibody, peptide, nucleic acid molecule, small molecule, mimetic or other pharmaceutically useful compound according to the present -invention that is to be given to an individual, administration is preferably in a "prophylactically effective amount" or a "therapeutically effective amount" (as the case may be, although prophylaxis may be considered therapy), this being sufficient to show benefit to the individual. The actual amount administered, and rate and time-course of administration, will depend on the nature and severity of what is being treated. Prescription of treatment, e.g. decisions on dosage etc, is within the responsibility of general practioners and other medical doctors.

A composition may be administered alone or in combination with other treatments, either simultaneously or sequentially dependent upon the condition to be treated.

Pharmaceutical compositions according to the present invention, and for use in accordance with the present invention, may include, in addition to active ingredient, a pharmaceutically acceptable excipient, carrier, buffer, stabiliser or other materials well known to those skilled in the art. Ouch materials should be non-toxic and should not interfere with the efficacy of the active ingredient. The precise nature of the carrier or other material will depend on the route of administration, which may be oral, or by injection, e.g. cutaneous, subcutaneous or intravenous.

Pharmaceutical compositions for oral administration may be in tablet, capsule, powder or liquid form. A tablet may include a solid carrier such as gelatin or an adjuvant. Liquid pharmaceutical compositions generally include a liquid carrier such as water, petroleum, animal or vegetable oils, mineral oil or synthetic oil. Physiological saline solution, dextrose or other saccharide solution or glycols such as ethylene glycol, propylene glycol or polyethylene glycol may be included.

For intravenous, cutaneous or subcutaneous injection, or injection at the site of affliction, the active ingredient will be in the form of a parenterally acceptable aqueous solution which is pyrogen-free and has suitable pH, isotonicity and stability. Those of relevant skill in the art are well able to prepare suitable solutions using, for example, isotonic vehicles such as Sodium Chloride Injection, Ringer's Injection, Lactated Ringer's Injection. Preservatives, stabilisers, buffers, antioxidants and/or other additives may be included, as required.

Liposomes, particularly cationic liposomes, may be used in carrier formulations.

Examples of techniques and protocols mentioned above can be found in Remington's Pharmaceutical Sciences, 16th edition, Osol, A. (ed), 1980.

The agent may be administered in a localised manner to a tumour site or other desired site or may be delivered in a manner in which it targets tumour or other cells.

Targeting therapies may be used to deliver the active agent more specifically to certain types of cell, by the use of targeting systems such as antibody or cell specific ligands. Targeting may be desirable for a variety of reasons, for example if the agent is unacceptably toxic, or if it would otherwise require too high a dosage, or if it would not otherwise be able to enter the target cells.

Instead of administering these agents directly, they may be produced in the target cells by expression from an encoding gene introduced into the cells, eg in a viral vector (a variant of the VDEPT technique—see below). The vector may targeted to the specific cells to be treated, or it may contain regulatory elements which are switched on more or less selectively by the target cells.

The agent (e.g. small molecule, mimetic) may be administered in a precursor form, for conversion to the active form by an activating agent produced in, or targeted to, the cells to be treated. This type of approach is sometimes known as ADEPT or VDEPT, the former involving targeting the activator to the cells by conjugation to a cell-specific antibody, while the latter involves producing the activator, e.g. an enzyme, in a vector by expression from encoding DNA in a viral vector (see for example, EP-A-415731 and WO 90/07936).

An agent may be administered in a form which is inactive but which is converted to an active form in the body. For instance, the agent may be phosphorylated (e.g. to improve solubility) with the phosphate being cleaved to provide an active form of the agent in the body.

A composition may be administered alone or in combination with other treatments, either simultaneously or sequentially dependent upon the condition to be treated, such as cancer or any other condition in which an effect on cell viability is desirable.

Nucleic acid according to the present invention, encoding a polypeptide or peptide able to modulate DNA replication, may be used in methods of gene therapy, for instance in treatment of individuals, e.g. with the aim of preventing or curing (wholly or partially) a disorder or for another purpose as discussed elsewhere herein.

Vectors such as viral vectors have been used in the prior art to introduce nucleic acid into a wide variety of different target cells. Typically the vectors are exposed to the target cells so that transfection can take place in a sufficient proportion of the cells to provide a useful therapeutic or prophylactic effect from the expression of the desired polypeptide. The transfected nucleic acid may be permanently incorporated into the genome of each of the targeted cells, providing long lasting effect, or alternatively the treatment may have to be repeated periodically.

A variety of vectors, both viral vectors and plasmid vectors, are known in the art, see U.S. Pat. No. 5,252,479 and WO 93/07282. In particular, a number of viruses have been used as gene transfer vectors, including papovaviruses, such as SV40, vaccinia virus, herpesviruses, including HSV and EBV, and retroviruses. Many gene therapy protocols in the prior art have used disabled murine retroviruses.

As an alternative to the use of viral vectors other known methods of introducing nucleic acid into cells includes electroporation, calcium phosphate co-precipitation, mechanical techniques such as microinjection, transfer mediated by liposomes and direct DNA uptake and receptor-mediated DNA transfer.

Receptor-mediated gene transfer, in which the nucleic acid is linked to a protein ligand via polylysine, with the ligand being specific for a receptor present on the surface of the target cells, is an example of a technique for specifically targeting nucleic acid to particular cells.

A polypeptide, peptide or other substance able to modlate or interfere with DNA replication or other substance as disclosed herein, or a nucleic acid molecule encoding a peptidyl such molecule, may be provided in a kit, e.g. sealed in a suitable container which protects its contents from the external environment. Such a kit may include instructions for use.

BRIEF DESCRIPTION OF THE FIGURES

FIG. 1A shows DNA synthesis in G1 and S phase nuclei in vitro. The percentages of nuclei that only incorporated biotin-dUTP in vitro (grey bars) and nuclei that incorporated both biotin-dUTP in vitro and BrdU in vivo (black bars)

were determined by fluorescence microscopy. Fluorescein-linked anti-BrdU antibody and TexasRed-linked streptavidin were used to detect label incorporated in vivo and in vitro, respectively. A total of $1.2 \times 10^6$ nuclei was used in each experiment and the ratios of S to G1 phase nuclei are indicated. The graph shows t of total nuclei replicating at different ratios of S:G1 nuclei.

FIG. 1B shows that S phase nuclei induce DNA synthesis in a dose dependent manner in co-incubated G1 nuclei in vitro. Data are expressed as percentages of G1 phase nuclei in the reaction that incorporated label only in vitro as specified under method (1) in Experimental Procedures. The graph shows % of G1 nuclei initiated at different ratios of S:G1 nuclei.

FIG. 2A: G1 phase nuclei were prepared at the indicated times after a release from mitosis and co-incubated with S phase nuclei at a 1:1 ratio in a cytosol from S-phase cells. The graph shows % of G1 nucleic initiated at different hours after entry into G1 (S phase nuclei constant).

FIG. 2B S phase nuclei were prepared at the indicated times after release from a block in very early S phase and co-incubated with G1 phase nuclei at a 1:1 ratio in a cytosol from S phase cells. The graph shows % G1 nuclei initiated at different hours after entry of S phase cells into S phase (G1 nuclei constant).

FIG. 2C: G1 and S phase nuclei were co-incubated at a 1:1 ratio in a cytosolic extract derived either from G1 or from S phase. The percentage of G1 phase nuclei that initiated DNA synthesis in the reaction was determined as in FIG. 1, as is shown for G1 and S phase cell cytosolic fraction.

FIG. 4A shows the results of experiments in which G1 phase nuclei were incubated in cytosolic extract derived from G1, S or G2 phase HeLa cells in the presence of an S phase nuclear extract. The percentage of G1 phase nuclei that initiated DNA synthesis in the reaction was determined as described under methods (1) and (2) in Experimental Procedures, and is plotted for G1, S and G2 phase cytosolic extract.

FIG. 4B: Titration of nuclear extracts. Nuclear extracts from G1, S and G2 phase cells were added at the indicated amounts ($\mu$l) to reactions containing G1 phase nuclei and S phase cytosolic extract and % of G1 nuclei initiated calculated and plotted on the graph.

FIG. 4C shows the time course of the initiation in vitro. Nuclear extracts (10 $\mu$l) from G1, S and G2 phase cells were added to reactions containing G1 phase nuclei and S phase cytosolic extract. Reactions were stopped at the indicated times (hours) and the % of G1 nuclei initiated plotted for each time.

FIG. 5. Efficiency of initiation varies with the precise cell cycle position of the substrate nuclei. Hela cells were synchronised at various times after entry into G1 phase and in G2 phase. G1 and G2 nuclei were prepared and incubated with nuclear and cytosolic extracts from S-phase cells. The indicated maximal percentages of nuclei that initiated DNA synthesis in vitro were determined after subtraction of S phase contaminants as specified under method (2) in Experimental Procedures and plotted at different times in hours after exit from M.

FIG. 6. Semiconservative DNA replication initiated in vitro. DNA synthesis was initiated by S phase nuclear and cytosolic extracts in G1 nuclei in the presence of BrdUTP and $\alpha P^{32}$-DATP. Buoyant CsCl density gradient centrifugation of DNA synthesised in vitro was performed. G1 phase nuclei were incubated in S phase cytosol with (panel a) and without (panel b) S phase nuclear extract for 2 h. The nuclear DNA was then treated with 0.2 U MNase and the purified DNA was separated on CsCl density gradients. The positions of hemisubstituted (HL) and unsubstituted DNA (LL) in the fractionated gradient are indicated. (kcpm per fraction is plotted for different fraction numbers)

FIG. 7A shows titration of recombinant cyclins and kinases to a reaction containing a cytosolic extract from S-phase cells and G1 phase nuclei as substrates. % of G1 nuclei initiated is plotted against $\mu$l of protein added.

FIG. 7B shows cross-titration of cyclins A and E, each complexed to Cdk2, to similar reactions. The percentage of G1 phase nuclei that initiated DNA synthesis in the reaction was determined as described under method (2) in Experimental Procedures and plotted for different ratios of cyclin A/cdk2:cyclin/ckd2 (1 $\mu$l protein).

We describe below the establishment of a novel cell-free system from somatic human cells that obeys somatic cell cycle controls. With this system, we analyse the factors that trigger the initiation of DNA replication in somatic cell nuclei.

A. Results

A.1 G1 phase nuclei initiate DNA synthesis when co-incubated with S phase nuclei and cytosol As an initial step to establish a human cell-free system for the initiation of DNA replication we sought to adapt permissive conditions observed in cell fusion experiments. In fusions between synchronised S and G1 or G2-phase cells only G1 phase nuclei, but not G2 phase nuclei, initiated DNA replication in the heterokaryon (Rao and Johnson, 1970). We therefore first synchronised HeLa cells in the G1 and S phases of the cell cycle and isolated nuclei from these cultures. Replicating DNA in these nuclei was pre-labelled with BrdU in vivo to allow a clear identification, by immunofluorescence microscopy, of nuclei that had been in S phase already. S and G1 phase nuclei were then incubated at defined nuclear ratios in a cytosolic extract prepared from S phase cells, supplemented with nucleoside and deoxynucleoside triphosphates. These reactions contained biotin- 16-dUTP as a marker for DNA synthesised during the in vitro incubation. Indirect fluorescent microscopy was used to determine the number of nuclei incorporating label in vivo and in vitro. We used this assay to distinguish nuclei that had initiated DNA synthesis in vivo and elongated synthesis in vitro (Heintz and Stillman, 1988; Krude, 1995) from nuclei that initiated DNA synthesis in vitro.

Figure 1A:
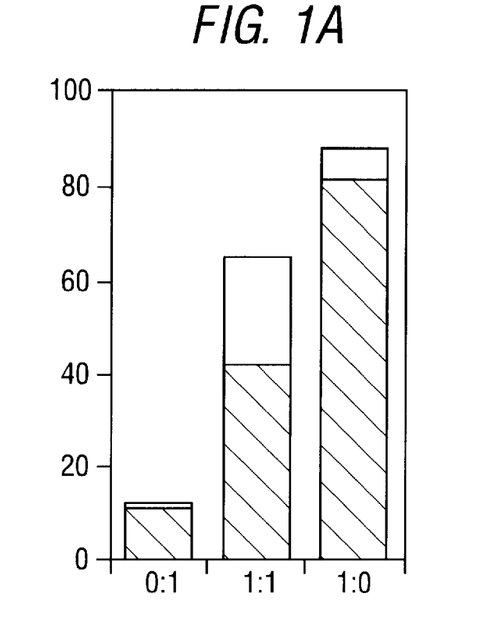
FIGS. 1A and 1B. Initiation of DNA synthesis in G1 phase nuclei co-incubated with S phase nuclei in a human S phase cell extract. HeLa cells were synchronised in the G1 and S phases of the cell cycle and nuclei were prepared as described under Experimental Procedures. Analysis of the cell cycle position of these nuclei was by flow cytometry.
Figure 1B:
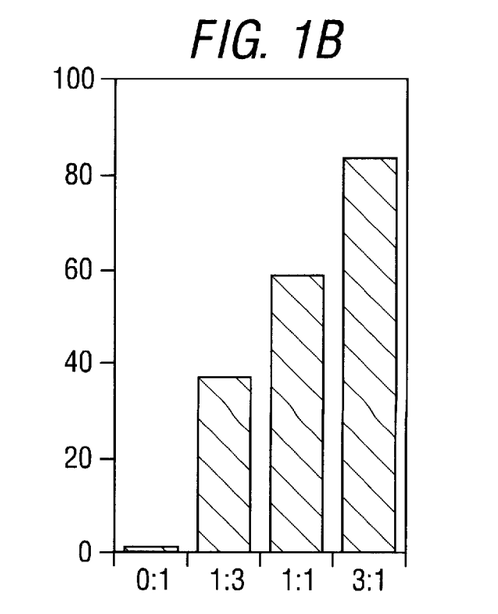

S phase nuclei efficiently elongated DNA replication (FIG. 1A) under these conditions. G1 nuclei incubated without added S phase nuclei did not initiate DNA replication to a significant extent in vitro (FIG. 1B). In contrast, a co-incubation of equal amounts of G1 phase nuclei with S phase nuclei led to the initiation of DNA synthesis in a significant fraction of the G1 phase nuclei (FIG. 1A). In every nucleus that initiated DNA synthesis in vitro, we observed a pattern of replication foci typical for early S phase, whereas nuclei that were already in S phase showed patterns of foci characteristic of later stages of S phase. We have considered the possibility that some nuclei synthesising DNA in vitro may in fact have initiated DNA replication in vivo, but not yet accumulated sufficient label for detection by immunofluorescent microscopy. These nuclei would then appear as false-positives. This possibility is excluded by experiments described below as explained in the discussion.

The efficiency of initiation of DNA synthesis in G1 nuclei was further analysed by varying the ratio between G1 and S phase nuclei. The number of G1 nuclei initiating in vitro depended clearly on the amount of co-replicating S phase nuclei (FIG. 1B). We conclude that replicating S phase nuclei export molecules that induce initiation of DNA synthesis in neighbouring G1 nuclei.

Figure 2A:
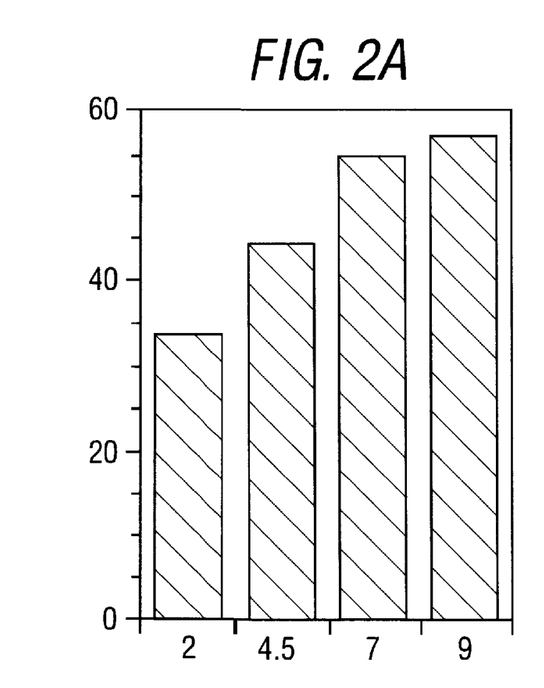
FIGS. 2A–2C. Cell cycle-specific induction of initiation of DNA synthesis in G1 phase nuclei. Hela cells were synchronised at various times after entry into the G1 and S phase and the nuclei were isolated. Analysis of the cell cycle position of these nuclei was by flow cytometry.
Figure 2B:
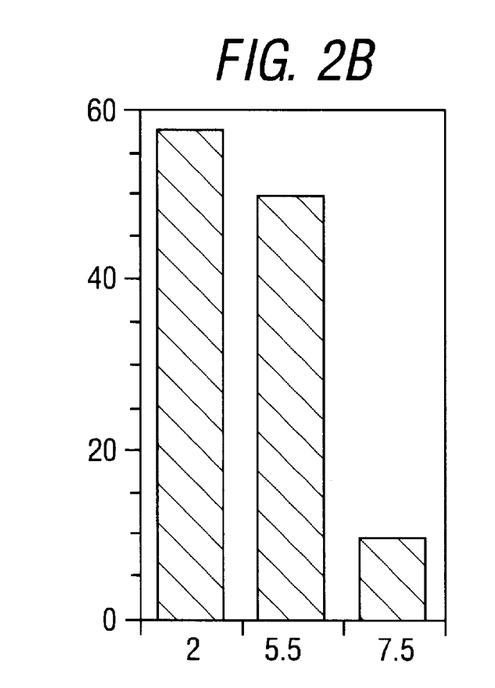

Next, we examined further the contributions of nuclei and cytosolic extract to the initiation of DNA synthesis in vitro (FIG. 2). First, we asked whether nuclei prepared at different times during progression through G1 phase were able to initiate DNA synthesis in vitro. Nuclei were prepared between 2 h and 9 h after release from mitosis. They were incubated with an identical number of S phase nuclei in a cytosolic extract from S phase cells. Nuclei from all stages of the G1 phase initiated DNA synthesis under these conditions, however, a higher proportion of nuclei prepared from later stages of G1 phase initiated DNA synthesis than nuclei from earlier stages of G1 (FIG. 2A). We then analysed whether the ability of S phase nuclei to trigger initiation in neighbouring G1 phase nuclei is restricted to a particular stage of the progression of S phase. Nuclei were prepared from cells 2 h, 5.5 h and 7.5 h after release from a block in very early S phase to obtain preparations of early, mid and late S phase nuclei. Early and mid S phase nuclei induced G1 nuclei to initiate DNA synthesis with similar efficiencies, late S phase nuclei were clearly less effective (FIG. 2B). Remarkably similar differences were observed in cell fusion experiments (Johnson and Mullinger, 1975).

Figure 2C:
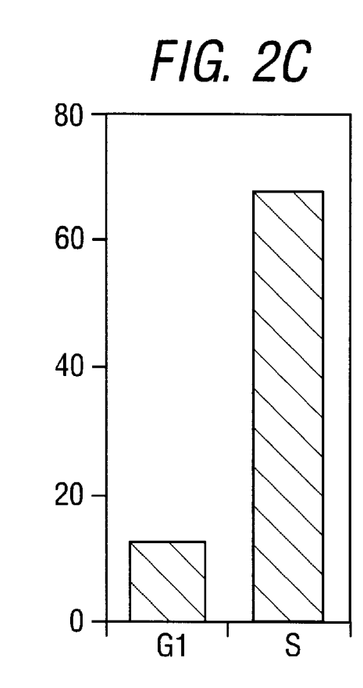

Finally, we addressed the contribution of the cytosolic extract to the initiation of DNA synthesis in vitro and prepared cytosolic extracts from cells synchronised in G1 and S phase. Both extracts permitted the elongation of DNA synthesis in S phase nuclei (data not shown). In contrast, only S phase, but not G1 phase cytosolic extracts supported efficient initiation of DNA synthesis in G1 nuclei on co-incubation with S phase nuclei (FIG. 2C).

A.2 G2 phase nuclei do not initiate DNA synthesis

Figure 3:
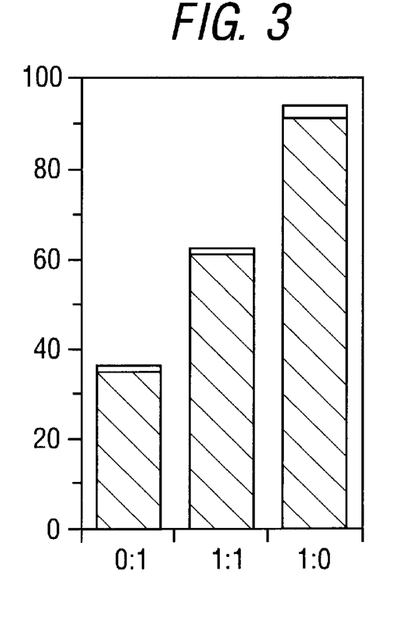
FIG. 3. G2 phase nuclei do not initiate DNA synthesis in vitro in the presence of S phase nuclei. HeLa cells were synchronised in the G2 and S phase of the cell cycle and the nuclei were isolated. Analysis of the cell cycle position of these nuclei was by flow cytometry. The figure shows DNA synthesis in G2 and S phase nuclei in vitro, plotting of total nuclei replicating at different ratios of S:G2 nuclei. The percentages of nuclei that only incorporated label in vitro (grey bars) and nuclei that incorporated label both in vitro and in vivo (black bars) were determined by indirect fluorescence microscopy.

We investigated the ability of S phase cytosol and nuclei to discriminate between unreplicated (G1) and replicated (G2) nuclei as substrates. Nuclei were isolated from cells synchronised in the G2 and S phases of the cell cycle and incubated at defined ratios in a cytosolic extract from S phase cells. The numbers of nuclei that synthesised If DNA in vivo, prior to preparation, and during the incubation in vitro were determined by fluorescence microscopy (FIG. 3). All S phase nuclei elongated DNA synthesis under these conditions. The preparation of G2 phase nuclei contained approximately 35% of late S phase contaminants that also continued DNA synthesis in vitro. Importantly, no initiation of DNA synthesis was observed in G2 phase nuclei co-incubated with S phase nuclei in a cytosolic S phase extract (FIG. 3). We therefore conclude that these in vitro incubations obey cell cycle controls. DNA synthesis initiates efficiently only in G1 nuclei, but not in G2 nuclei.

In summary, the co-incubation experiments described above clearly demonstrate that it is possible to reconstruct in vitro the conditions that initiate human DNA synthesis specifically in G1, but not in G2 nuclei (Rao and Johnson, 1970).

Figure 4A:
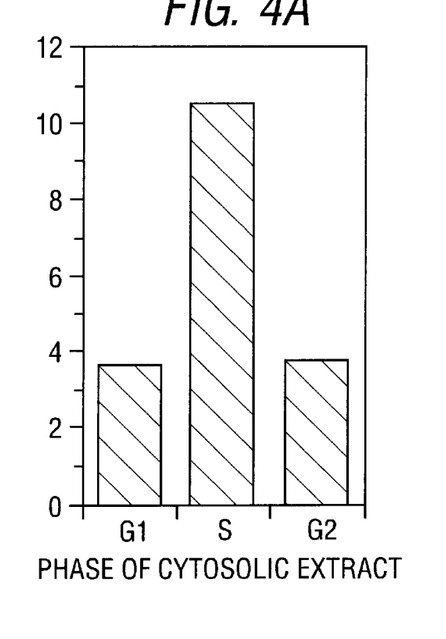
FIGS. 4A–4C. Initiation of DNA synthesis in vitro in the presence of a soluble nuclear extract from S phase cells. Nuclear and cytosolic extracts from cells synchronised in the G1, S and G2 phases were prepared. G1 phase nuclei were incubated in the extracts without added S phase nuclei and the percentage of nuclei that initiated DNA synthesis in vitro was determined by fluorescence microscopy.
Figure 4B:
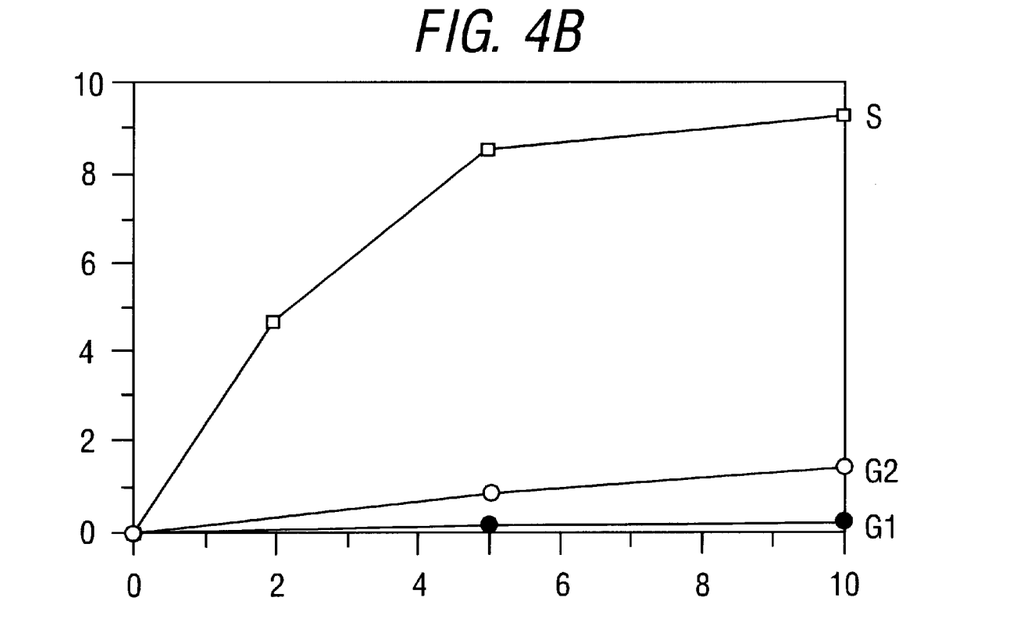
Figure 4C:
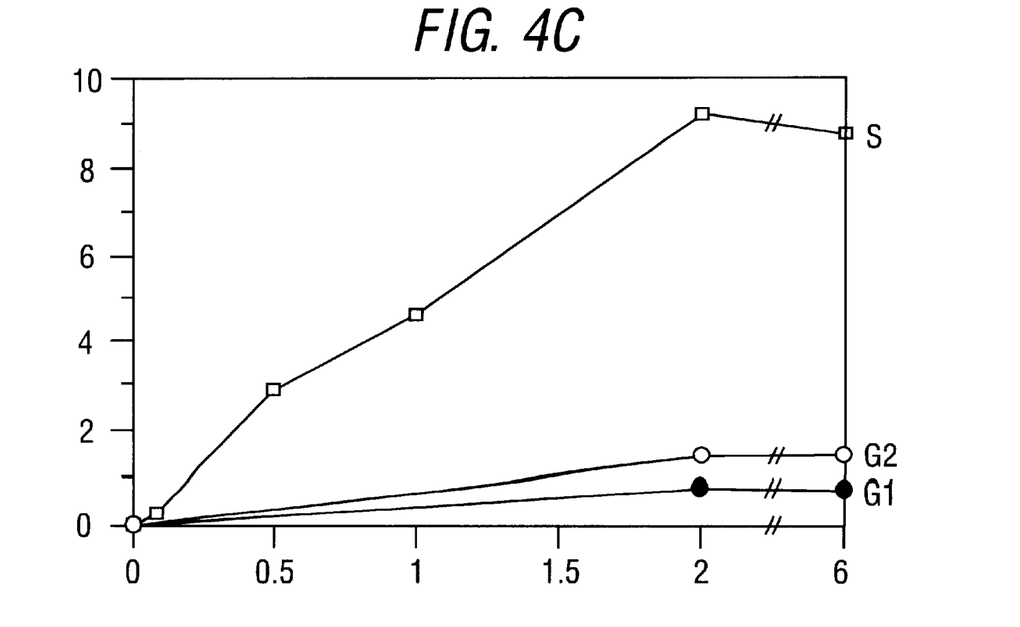

A.3 S phase nuclear extracts can replace S phase nuclei, initiating DNA synthesis in G1, but not in G2 phase nuclei To reduce the complexity of the system we replaced the inducing S-phase nuclei with soluble nuclear extract from S phase cells. When this was added to reactions containing G1 phase nuclei and S phase cytosolic extract, DNA synthesis initiated in some G1 phase nuclei. This initiation also depended on the cytosolic extract from S-phase cells, as cytosolic extracts from G1 or G2 phase cells did not allow efficient initiation of DNA synthesis in the presence of the nuclear extract from S phase cells (FIG. 4A). Addition of increasing amounts of nuclear extract from S phase, but not from G1 or G2 phase cells, lead to a dose-dependent increase of G1 nuclei initiating DNA synthesis in vitro (FIG. 4B). During this reaction, the percentage of G1 phase nuclei that initiated DNA synthesis increased linearly for about two hours (FIG. 4C).

Figure 5:
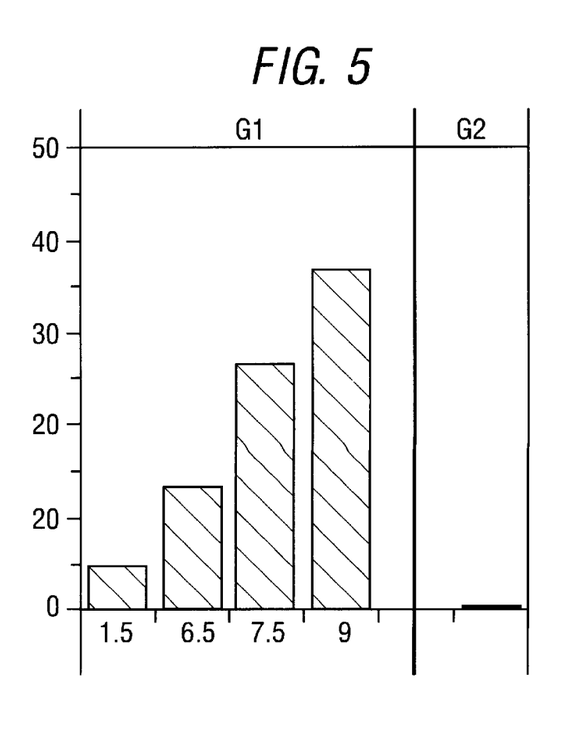

The maximal percentage of G1 phase nuclei initiating in vitro varied between different preparations of nuclei (data not shown). It could not be increased by higher concentrations of nuclear extract or by longer incubations (FIGS. 4B and C). To test whether this number correlated with any stage of G1 phase progression, we prepared nuclei from cells synchronised in G1 phase at different times after release from mitosis. The maximal percentage in G1 phase nuclei initiating in vitro clearly increased during the progression of G1 phase and maximal efficiencies were obtained at late stages of G1 phase (FIG. 5). Importantly, nuclei prepared from G2 phase cells did not initiate DNA synthesis at all (FIG. 5).

We next quantitated the amount of DNA synthesis in this system by measuring the incorporation of $\alpha^{32}$ P-dAMP's into nuclear DNA (Table 1). S phase nuclei efficiently elongated pre-existing DNA synthesis in vitro. After 2 h incubation S phase nuclei had synthesised about 10% of their diploid genomic DNA content, which is equivalent to about 50% of the replication rate observed in vivo [Table 1, (a)]. Without S phase nuclear extract G1 nuclei only supported elongation in the contaminating S phase nuclei (see FIG. 1), albeit at a slightly reduced efficiency [Table 1, (b)]. In the presence of an S phase nuclear extract, DNA synthesis was initiated in about 100% of the G1 nuclei in vitro and the efficiency of this additional DNA synthesis within each nucleus in the 2 h incubation was comparable with that of S phase nuclei that had initiated in vivo [Table 1, (c) and (d)]. We conclude that G1 nuclei initiate DNA synthesis in the presence of nuclear and cytosolic extracts from S phase cells in vitro and elongate at the same rate (about 50% of the in vivo rate) as in pre-initiated S phase nuclei.

Figure 6A:
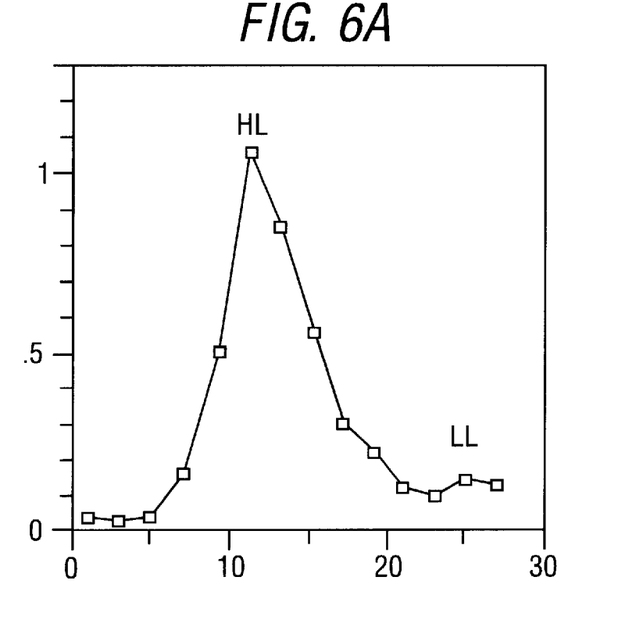
Figure 6B:
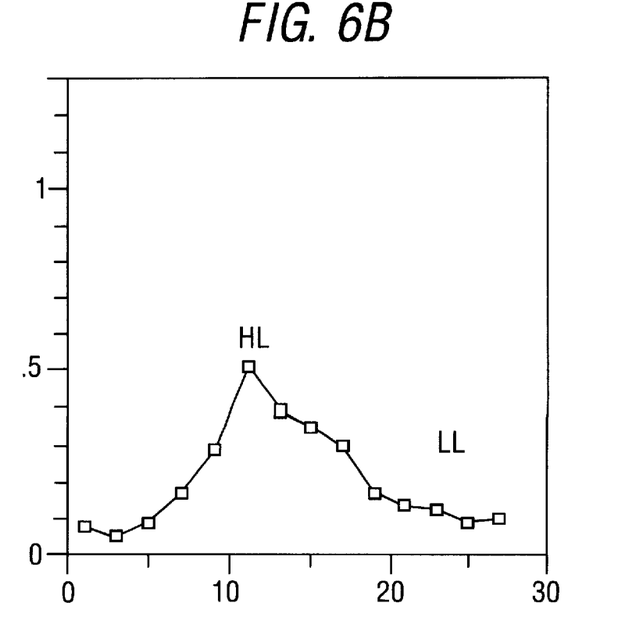

A.4 S phase nuclear extract triggers semiconservative DNA replication in G1 nuclei To confirm that DNA synthesised after initiation in vitro is due to semiconservative DNA replication we used BrdU-substitution and density gradient centrifugation. G1 nuclei were incubated in cytosolic and nuclear extracts from S phase cells in the presence of BrdUTP and radioactively labelled DATP. After a 2 h incubation genomic DNA was treated with micrococcal nuclease (MNase) to generate defined DNA fragments of mono- and polynucleosomal length. After a 2 h incubation, nuclei were treated with 0 U, 0.1 U, 0.3 U, or 1 U MNase for 10 min and the treated DNA was analysed by gel electrophoresis and autoradiography. This also indicated that DNA synthesised in vitro is assembled into chromatin consisting of regularly spaced nucleosomes. Density gradient centrifugation of this polynucleosomal genomic DNA showed that DNA synthesised with and without S phase nuclear extract was hemisubstituted with BrdU (FIG. 6). Importantly, the additional DNA synthesis observed after in vitro initiation in the presence of the S phase nuclear extract was clearly of hemisubstituted (HL) density (FIG. 6, panel a). These data show that this system initiates (and further elongates) semiconservative DNA replication in extracts from human cells.

A.5 S phase cyclins and Cdk2 replace nuclear extract and trigger initiation of DNA synthesis in G1 phase nuclei Control experiments indicated that initiation, but not elongation, of DNA replication in G1 nuclei incubated as above is completely inhibited by the kinase inhibitor 6-DMAP at a 3 mM concentration (data not shown). We therefore tried to replace the initiating nuclear extract from S-phase cells with preparations of recombinant human cyclins and their cognate cyclin-dependent kinases (Cdk's). Preliminary experiments showed that the S phase nuclear extract contained histone H1 kinase activity and cyclin A (data not shown).

Figure 7A:
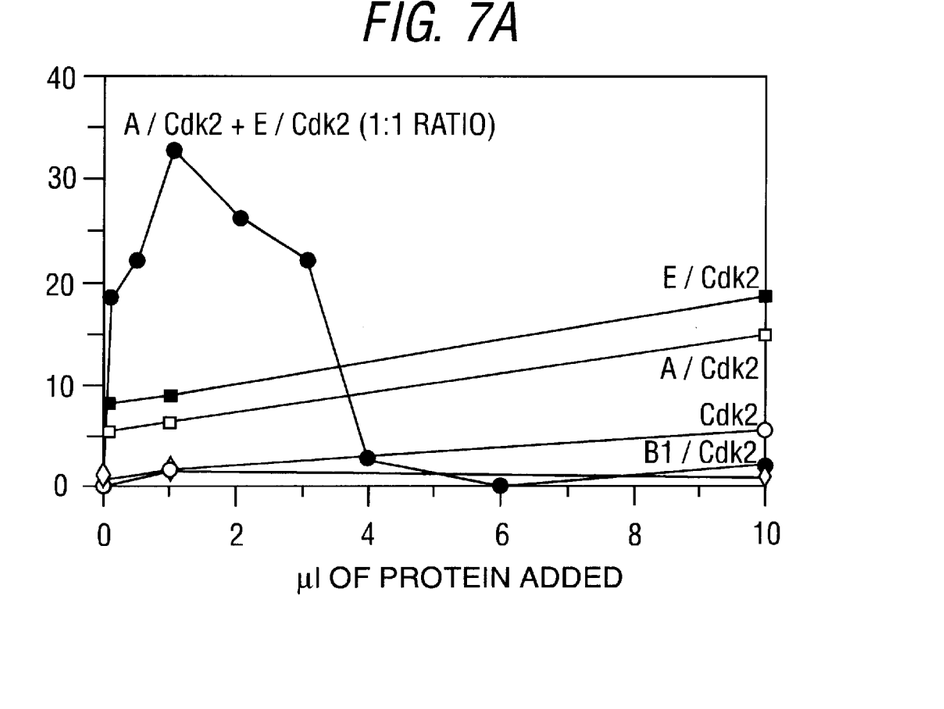
FIGS. 7A and 7B. Cyclins A and E, complexed to Cdk2, initiate DNA synthesis in vitro. Recombinant human cyclins E, A and B1 were co-expressed with their kinase partners Cdk2 and Cdc2 and purified as specified under Experimental Procedures.
Figure 7B:
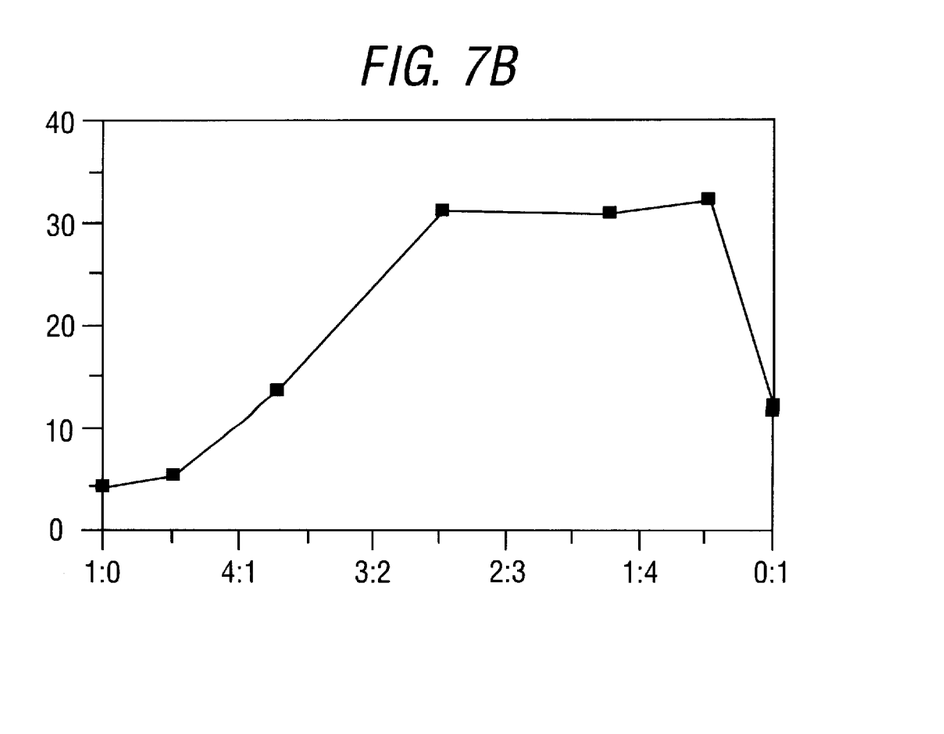

We expressed human Cdk2 alone or complexed to S phase cyclins A and E and, as a control, mitotic cyclin B1 complexed to Cdc2. These preparations were added to reactions containing G1 phase nuclei and cytosolic extract from S phase cells in the absence of nuclear extract. The percentages of G1 nuclei initiating DNA replication were monitored by fluorescence microscopy (FIG. 7). Mitotic cyclin B1/Cdc2 and the kinase Cdk2 alone did not trigger initiation of DNA synthesis in vitro (FIG. 7A). However, each of the S phase cyclins A and E, complexed to Cdk2, induced DNA synthesis moderately efficiently (FIG. 7A). Importantly, a combination of both cyclins A and E complexed to Cdk2, initiated DNA synthesis synergistically at the maximal efficiency (FIG. 7A, B) observed with an S phase nuclear extract (see FIG. 5). Addition of the nuclear extract to optimal concentrations of both cyclins did not increase the efficiency of in vitro initiation (data not shown). Furthermore, higher concentrations of both cyclins A and E, complexed to Cdk2, together led to an inhibition of the initiation in vitro in a dose-dependent manner (FIG. 7A), suggesting a negative feedback control mechanism.

We conclude that the S-phase promoting cyclins A and E, both complexed to their cognate kinase Cdk2, trigger the initiation of DNA synthesis in G1 nuclei in vitro.

B. Experimental Procedures

B.1 Cell culture and synchronisation

HeLa-S3 cells were cultured as exponentially growing subconfluent monolayers on 145 mm plates in DME-medium (Gibco), supplemented with 5% foetal calf serum (Gibco), 10 U/ml penicillin (Sigma) and 0.1 mg/ml streptomycin (Sigma).

To prepare S phase nuclei or extracts, cells were synchronised in S phase by a single block in culture medium containing 2.5 mM thymidine (Sigma) for 25 hours (Rao and Johnson, 1970), followed by a release into culture medium for 2 h. To prepare very early S phase nuclei, two sequential 25 h-blocks in 2.5 mm thymidine were used, separated by a 12 hour interval without thymidine (Rao and Johnson, 1970). Cells at various specific stages of S phase were obtained by releasing very early S phase cells into culture medium for the times indicated under results. Cells were synchronised in G2 phase by releasing cells blocked in very early S phase into culture medium for 9–10 h. Transit into G1 was inhibited by adding 40 ng/ml nocodazole (Sigma) to the culture medium for 5 h prior to preparation. Accumulating mitotic cells were removed from the preparation of G2 nuclei by selective detachment during the washes in hypotonic buffer (see below). Cells in the G1 phase were obtained by releasing cells blocked in very early S phase into culture medium for 3 hours, followed by adding 40 ng/ml nocodazole (Sigma) to the culture medium for an additional 12 hours to arrest them in mitosis (Johnson et al., 1993). These mitotic cells were then released into fresh culture medium for 6 h, unless otherwise indicated.

Cell synchronisation was determined by flow cytometry of isolated nuclei. One million nuclei directly stained with propidium iodide (5 $\mu$g/ml in PBS containing 0.4% Triton X-100) and analysed by FACScan (Becton Dickinson) and the Lysis II-software. Data are presented as histograms showing relative DNA content (x-axis) and cell number (y axis).

B.2 Preparation of nuclei

Nuclei were prepared as described (Heintz and Stillman, 1988; Krude, 1995) with minor modifications: Cells were washed twice with ice-cold hypotonic buffer (20 mM potassium-HEPES; pH 7.8; 5 mM potassium acetate, 0.5 mM $MgCl_2$, 0.5 mM DTT). All subsequent steps were carried out at $4_tC$. Cells were allowed to swell for 10 minutes in 20 ml hypotonic buffer per plate, and excess buffer was removed. At this stage, mitotic cells were removed, because they detached from the substratum under hypotonic conditions. Interphase cells still attaching to the substratum were scraped off the plates and disrupted with 25 strokes in a dounce homogeniser (Wheaton), using a loose fit pestle. Nuclei were pelleted at 4000 rpm for 5 min in an Eppendorf 5415C centrifuge. The supernatant was used for a preparation of the cytosolic extract. Pelleted nuclei were resuspended and washed three times in PBS and finally pelleted at 5000 rpm for 5 min. Excess supernatant was removed and pelleted nuclei were resuspended in the residual volume. Concentrations of nuclei were determined with a hemocytometer.

B.3 Preparation of cell-free extracts

Cytosolic supernatant from the preparation of nuclei was re-centrifuged at 20,000× g in a Sorvall SS34 rotor for 30 min and frozen in liquid $N_2$. Cytosolic extracts contained about 9–11 $\mu$g/$\mu$l protein, determined with a Bio-Rad kit (Bradford, 1976) and bovine serum albumin as a standard.

For the preparation of nuclear extracts pelleted nuclei were resuspended in hypotonic buffer containing 0.4M NaCl at $1.5 \times 10^8$ nuclei/ml. Nuclear proteins were extracted for 90 min at $4_tC$. Nuclear material was pelleted for 30 min at 14,000 rpm in an Eppendorf 5415C centrifuge. The supernatant was directly used and freshly prepared for each experiment. Nuclear extracts contained 7–9 $\mu$g/$\mu$l protein.

These extracts were apparently free of nuclei since residual nuclear material in the extracts could not be detected by microscopy (not shown).

B.4 Preparation of recombinant baculoviruses

Polymerase chain reaction (PCR) was used to add a six histidine (His6) affinity epitope to the carboxyl-terminus of human cdc2 and CDK2 (Lee and Nurse, 1987; Tsai et al, 1991) cDNAs. The cdc2 and CDK2 cDNAs were cloned into the Xma I and Spe I sites of the baculovirus expression vector pAcA4 (Belyaev and Roy, 1993). Human cyclin A and cyclin B1 (Pines and Hunter, 1989; Pines and Hunter, 1990) were cloned into the Xba I and BGl II sites of pAcA4. Human cyclin E (Koff et al, 1991) was cloned into the pVL941 baculovirus expression vector. Recombinant baculoviruses were generated using the Baculogold™ system from PharMingen (San Diego, Calif.).

B.5 Expression and partial purification of human cyclin/Cdk complexes

To express human cyclin A/Cdk2, cyclin E/Cdk2 and cyclin B1/Cdc2 complexes, Sf9 insect cells were co-infected with the cyclin A and Cdk2, cyclin E and Cdk2, cyclin B1 and Cdc2 recombinant baculoviruses, respectively, at a multiplicity of infection of 5 for each recombinant baculovirus. Each cyclin/Cdk complex was purified from an 800 ml infected cell culture ($1.5 \times 10^9$ cells) using a $Ni^{2+}$ affinity column to isolate complexes containing Cdk2 or Cdc2. Infected insect cell cultures were harvested 60 h post infection, washed in 10 mM Hepes NaOH pH 7.4, 150 mM NaCl, 1 mM EDTA and lysed in ice cold lysis buffer (10 mM Hepes NaOH pH 7.4, 25 mM NaCl, 1 mM EDTA, 1 mM PMSF, 1 mg/ml leupeptin, antipain, chymostatin A, and pepstatin A) by dounce homogenisation. Immediately following homogenisation NaCl in the lysate was adjusted to 0.3 M. Lysates were cleared by spinning at 20,000× g for 15 min and then at 100,000× g for 30 min, 5 mM $MgCl_2$ was then added to the resulting supernatant, before passing by gravity through Ni 2+NTA-agarose affinity columns (0.5 ml; Qiagen). After loading Ni 2+-NTA columns with supernatant the columns were washed with 50 column volumes of wash buffer (10 mM Hepes pH 7.4, 0.5 M NaCl, 10% v/v glycerol, 5 mM imidazole, 1 mM PMSF). Bound proteins were eluted with 50 mM imidazole in wash buffer. Cyclin/Cdk(his)$_6$ complexes were separated from monomeric Cdk(his)$_6$ and other contaminants by injecting imidazole eluate into a Sephacryl S-200 26/60 gel filtration column (Pharmacia) that had been pre-equilibrated with gel filtration buffer (25 mM Hepes NaoH pH 7.5, 200 mM NaCl, 1 mM EDTA 10% v/v glycerol). Gel filtration fractions were assayed for H1-histone activity by carrying out H1 histone kinase reactions as described in (Jackman et al., 1995). Histone H1 phosphorylation was measured using phosphocellulose filters (Pierce) and determining Cerenkov counts in a scintillation counter.

As a control, negligible amounts of H1-histone kinase activity were detected in identically isolated fractions from lysates of Sf9 cells that had been infected with wild type baculovirus or Cdc2/Cdk2 recombinant baculoviruses, indicating that H1-histone kinase activity in gel filtration fractions was due to expression of human cyclin-Cdk's. Histone H1 kinase activities of gel filtration elution profiles indicated that cyclin A/Cdk2 and cyclin B1/Cdc2 migrated at a volume corresponding to a MW of approximately 150 kDa. This is in close agreement with the elution volume of purifed cyclin A/Cdk2 and cyclin B1/Cdc2 complexes (160 kDa) obtained by (Desai et al., 1992). Cyclin E/Cdk2 migrated as a complex of approximately 140 kDa. Western blot analysis showed the presence of the relevant cyclin in each of the partially purified cyclin-Cdk complexes and confirmed that each partially purified cyclin-Cdk complex contained only one human cyclin (data not shown).

By measuring the specific activities of partially purified cyclin-Cdk complexes and comparing them to those obtained from measuring the histone H1 kinase activity of the lysate supernatants, this purification protocol resulted in an enrichment of cyclin/Cdk activity of approximately 50,000 for each cyclin/Cdk from infected insect cell lysates. The specific activities of our partially purified cyclin B1/Cdc2 (2.5 nmol/min/mg) and cyclin A/Cdk2 (6.2 nmol/min/mg) found by co-infecting insect cells are approximately 10 fold greater than those described for cyclin B1/Cdc2 and cyclin A/Cdk2, found following mixing purified cyclins with their Cdk partner in vitro and activating kinase activity by incubating with insect cell lysate (Desai et al., 1992). Partially purified cyclin E/Cdk2 had a specific histone H1 kinase activity of 0.3 nmol/min/mg.

Fractions containing cyclin-dependent histone H1 kinase activity were frozen in liquid $N_2$ and stored at –80 C after BSA had been added to a concentration of 5 mg/ml.

B.6 DNA synthesis reactions in vitro

Standard nuclear DNA synthesis reactions contained 30 $\mu$l of cytosolic extracts and up to 10 $\mu$l of nuclear extract or of a preparation of recombinant proteins. When smaller volumes were used, the remaining volume was adjusted to the final 10 $\mu$l by extraction buffer. Reactions further contained 10 $\mu$l of a buffered nucleotide-mix [yielding final concentrations of: 40 mM KDHEPES, pH 7.8 ; 7 mM $MgCl_2$; 3 mM ATP; 0.1 MM each of GTP, CTP, UTP; 0.1 mM each of DATP, dGTP and dCTP; 0.25 $\mu$M biotin-16-dUTP, 0.5 mM DTT; 40 mM creatine phosphate; 5 $\mu$g phosphocreatine kinase (all Boehringer Mannheim)]. In nuclear co-incubation experiments $1 \times 10^6$ nuclei were used as specified and in other experiments $0.4$–$0.6 \times 10^5$ nuclei were used as substrates. For a quantitation of nuclear DNA synthesis reactions also contained 1–2 $\mu$Ci $\alpha P^{32}$-DATP and biotin-16-dUTP was replaced by 0.1 mM dTTP, or, for density substitutions, by 0.1 mM BrdUTP (Sigma). Reactions were mixed on ice and started by transferring to 37 C. Standard incubation time was 2 h, unless stated otherwise. For fluorescence microscopy, reactions were stopped by diluting with 500 $\mu$l PBS at room temperature and were processed as specified below. For quantitation of DNA synthesis, reactions were blotted onto GF/C glass fibre filters, nucleic acids were precipitated in 10% TCA, washed and the incorporated radioactive dNMPs were determined by scintillation counting.

B.7 Analysis of reaction products

Fluorescent labelling and fluorescence microscopy were performed exactly as described (Krude, 1995), using Hoechst 33258 to visualise total DNA, fluorescein-conjugated antibodies to visualise BrdU-substituted DNA synthesised in vivo and Texas red conjugated streptavidin to visualise biotinylated DNA synthesised in vitro. For each experiment, more than a thousand nuclei were scored to achieve statistical significance.

The percentages of nuclei initiated in the in vitro reaction were calculated by the following equation:

$$\text{percentage of nuclei initiated} = \frac{P_{vitro} - P_S}{100 - P_S} \times 100\%$$

where $P_{vitro}$ is the percentage of all nuclei incorporating label in vitro, and $P_S$ is the percentage of nuclei in the reaction that were already in S phase. $P_S$ was determined either by in vivo-prelabelling [method (1)], or by subtracting from $P_{vitro}$ of the reaction, $P_{vitro}$ of a control reaction that allowed only elongation of replication in G1 phase cytosol in the absence of nuclear extracts or cyclin-Cdk complexes

[method (2)]. In control experiments, both methods yielded identical results. For each experiment the method used is specified in the figure legend. These calculations are derived from those used in cell fusion studies (Rao and Johnson, 1970).

Treatment of replication reactions with MNase (Boehringer Mannheim) was performed as described (Shimamura et al., 1988). Nuclease-resistant DNA was separated on 1.5% agarose gels in TAE buffer (Sambrook et al., 1989) and visualised by autoradiography of the dried gel. Density gradient centrifugation of MNase-treated DNA was performed as detailed previously (Blow and Laskey, 1986; Leno et al., 1992).

C. Discussion

In the experiments reported above, we used extracts and nuclei from synchronised cells to establish a human cell-free system that initiates DNA replication under cell cycle control. Nuclei from G1 phase, but not from G2 phase HeLa cells initiated DNA replication in vitro. This reaction depended on both cytosolic and nuclear factors from S-phase cells. The latter could be replaced functionally by recombinant human cyclins A and E complexed to Cdk2.

C.1 Evidence for initiation of DNA synthesis in vitro

We used fluorescence microscopy to visualise DNA replication in individual nuclei in vitro. As reported previously, S phase nuclei continued elongating DNA replication efficiently in vitro (Heintz and Stillman, 1988; Krude, 1995). These S phase nuclei were identified by prelabelling replicating DNA in vivo before preparing the nuclei. A different label was used to identify nuclei that incorporated label in vitro. Nuclei labelled in vitro, but not in vivo were designated as having initiated DNA synthesis in vitro. A proportion of nuclei may in fact have initiated DNA replication in vivo, but not yet accumulated sufficient label for detection by immunofluorescent microscopy. These nuclei would then appear as false-positives, but they cannot account for the in vitro initiation described above for the following reasons: First, in a time course experiment, their percentage should be constant and should not increase with time in vitro, because label is clearly detectable after only 5 to 10 minutes of the in vitro incubation (Krude, 1995). The percentage of the G1 nuclei initiating DNA synthesis in vitro increased linearly over the entire incubation period until the maximal efficiencies of up to 85% were reached after 2 hours (FIG. 4; and data not shown for the co-incubation experiments). On the other hand, a preparation of G1 nuclei contained less than 1% of nuclei that could be designated as having initiated DNA synthesis in vitro by these criteria (FIG. 1A). Second, addition of nuclear extract (and of recombinant cyclin-Cdk2 complexes) induced a dose-dependent increase in the percentage of nuclei initiating DNA synthesis in vitro above a constant background of S phase nuclei, present as contaminants from the synchronisation procedure (FIGS. 4 and 7). Third, only the initiation of DNA synthesis in G1 nuclei, but not the elongation in S phase nuclei was inhibited by 3 mM 6-DMAP (data not shown). Therefore, we conclude that those nuclei that incorporated label only in vitro, and not in vivo, initiated DNA synthesis in vitro and that false-positives occur at very low abundance of less than 1% of the G1 nuclei analysed.

C.2 Initiation of semiconservative DNA replication in vitro

In this system, several lines of evidence indicate that the DNA synthesis initiated in G1 nuclei is due to true semiconservative DNA replication, and not to DNA repair. First, in density substitution experiments, DNA synthesised in G1 nuclei after initiation in vitro was hemisubstituted with BrdU, as was the DNA synthesised in elongating S phase nuclei under identical conditions (FIG. 6). Second, the rate and amount of DNA synthesised per G1 nucleus after initiation in vitro was almost identical to the rate and amount of DNA synthesised per elongating S phase nucleus (Table 1). This DNA synthesis was inhibited by 30 $\mu$g/ml aphidicolin, an inhibitor of DNA polymerases $\alpha$ and $\delta$ (not shown) and furthermore, DNA replicated in vitro was efficiently assembled into chromatin (FIG. 6), excluding mitochondria or contaminating bacteria as substrates for this DNA synthesis [e.g. see: (Heintz and Stillman, 1988)]. Third, the DNA synthesised in a G1 nucleus after initiation in vitro was always localised at discrete subnuclear replication foci in a pattern typical for early S phase in human cells (Nakamura et al., 1984; Nakayasu and Berezney, 1989; Krude, 1995; Krude et al., 1996) (FIG. 1; and data not shown). On the other hand, S phase nuclei elongating in vitro continued DNA synthesis at subnuclear replication foci that were active in vivo, prior to the preparation (Krude, 1995). In these nuclei, patterns of replication foci were typical for all stages of S-phase, including mid and late S [see e.g. (Nakayasu and Berezney, 1989; Krude et al., 1996) for references]. During the in vitro incubation these active replication foci moved relative to their sites of prelabelling in vivo prior to the preparation (FIG. 1), as described for their dynamic behaviour in vivo (Manders et al., 1992). Taken together, these data indicate that DNA synthesis initiated in vitro is semiconservative DNA replication with dynamic and morphological characteristics of early S phase.

C.3 Factors required for initiation in vitro

The experimental conditions of this human system were adapted from cell fusion experiments where DNA replication is initiated under cell cycle control in a nucleus from a G1 phase, but not from a G2 phase cell, upon fusion with S phase cells (Rao and Johnson, 1970). We isolated nuclei from synchronised human cells and co-incubated either G1 or G2 nuclei with S phase nuclei in cytosolic extracts from synchronised cells. These cytosolic extracts elongate DNA replication in S phase nuclei (Heintz and Stillman, 1988; Krude, 1995) and also support SV40 DNA replication (Li and Kelly, 1984; D'Urso et al., 1990). Importantly, initiation of DNA synthesis in G1 phase, but not in G2 phase nuclei was triggered by a signal derived from S phase nuclei. This signal persisted through S phase, although with a reduced efficiency in late S (FIG. 2; and data not shown), as seen in cell fusion experiments (Johnson and Mullinger, 1975). This signal can be functionally replaced by a soluble nuclear extract from S-phase cells and, with the same efficiency, by recombinant human cyclins A and E complexed to Cdk2 (see below). These proteins are predominantly nuclear during G1 and S phase (Girard et al., 1991; Pines and Hunter, 1991; Dulic et al., 1992; Koff et al., 1992; Pagano et al., 1992; Rosenblatt et al., 1992; Cardoso et al., 1993; Ohtsubo et al., 1995). Taken together, these data indicate that at least one signal triggering the initiation of DNA synthesis in G1 nuclei in vitro is derived from an S phase nuclear structure, and not from the S phase cytosol as speculated before (Rao and Johnson, 1970; Heichman and Roberts, 1994). On the other hand, the cytosol from S phase, but not from G1 or G2 phase cells, contributes factors to the reaction that permit initiation to occur but that are not sufficient to initiate DNA synthesis on their own. The dependence of replication initiation on the cell cycle phases of the system components is therefore more complex than for initiation of SV40 DNA replication (D'Urso et al., 1990). For SV40 DNA, a cytosolic extract from human S phase cells, or a G1 phase extract supplemented with heterologous cyclin A/Cdc2 or cyclin B/Cdc2, is sufficient to initiate DNA replication in the presence of the viral initiator protein T antigen (D'Urso et al., 1990). For initiating DNA synthesis in G1 nuclei in the absence of exogenous viral factors, S phase cytosol is not sufficient, but only permissive. The basis for this permissiveness is unknown, but it is most likely that the S phase cytosol contains active replication factors synthesised and/or activated only in S phase, which are required to assemble initiation and replication complexes in G1 nuclei. However, the elongation of DNA replication in S-phase nuclei pre-initiated in vivo did not depend on S phase extracts. It was observed in cytosolic and nuclear extracts from G1, S and G2 cells and in the absence of nuclear extract, consistent with previous reports (Heintz and Stillman, 1988; Krude, 1995).

Importantly, G2 nuclei did not re-initiate DNA synthesis in this system. Therefore, extracts from human cells are capable of differentiating between nuclei according to their stage in the cell cycle. This is consistent with results obtained in the cell-free DNA replication system from *Xenopus laevis* eggs using human G1 and G2 cell nuclei (Leno et al., 1992.). However, these two systems are fundamentally different; in early Xenopus embryogenesis, very rapid S-phase alternates with mitosis in the absence of G1 and G2 phases. The control of these events is mimicked in extracts from activated Xenopus eggs by maternal proteins deposited in the egg and activated during fertilisation (Lohka and Masui, 1983; Blow and Laskey, 1986; Hutchison et al., 1987; Murray and Kirschner, 1989). After the midblastula transition, the embryonic cell cycle slows down and G1 and G2 phases are introduced into the cell cycle together with the control of the G1-to-S and G2-to-M transitions. Extracts and nuclei from human somatic cells used in this study therefore appear to reflect more closely the activities operating in the G1-to-S phase control than extracts from Xenopus eggs. We are currently comparing directly the human with the Xenopus system to identify differences in the regulation of early amphibian and somatic mammalian cell cycles.

C.4 Efficiency of initiation of DNA replication in G1 nuclei in vitro

This cell-free replication system enabled us to investigate contributions of the G1 phase of the cell cycle to the initiation of DNA replication in vitro. The maximal ability of G1 nuclei to initiate correlated with the position in G1 phase at the time of their preparation (FIGS. 2 and 4). It was relatively low in early G1 and increased to maximal levels at late stages of G1. However, a significant difference in this efficiency was detected with the two experimental approaches described in this paper: In co-incubation experiments up to 50% of early G1 nuclei initiated. For late G1 this value was as high as 85% (FIG. 2, and data not shown). In contrast, in the soluble systems the efficiencies were less than 5% for early G1 nuclei and up to 35% for late G1 (FIGS. 4 and 7). These differences in efficiency of initiation in vitro could be due to the following reasons:

First, G1 phase nuclei triggered by cyclin-Cdk2 complexes to initiate in vitro could be derived from from a subpopulation of cells that passed a restriction point in mid G1 in vivo and are hence already committed to enter S phase in response to inducing signals (Zetterberg et al., 1995). This subpopulation would increase in the population of G1 cells as they progress through G1. We are currently testing cyclin D and its cognate kinases for a role in this progression. In a second model, S phase nuclei, but not the soluble extracts and the recombinant proteins, could sequester or inactivate a hypothetical inhibitor(s) of the initiation of DNA replication that is associated with early, and to a lesser extent, with late G1 nuclei. This hypothetical inhibitor(s) could be one or more of the known inhibitors of G1 cyclins and their Cdks, such as $p21^{Cip1}$, $p27^{Kip1}$, or proteins encoded by the INK4 gene family (reviewed by (Draetta, 1994; Sherr, 1994; Sherr and Roberts, 1995); or they could be related to yeast $p40^{Sic1}$ (Nugroho and Mendenhall, 1994; Schwob et al., 1994). However, this possibility has to be treated cautiously, since an addition of excess recombinant cyclins A/Cdk2 and/or E/Cdk2 did not stimulate the efficiency of early G1 nuclei to initiate in vitro (FIG. 7; and data not shown), whereas overexpression of G1 cyclins in vivo could alleviate inhibitor-mediated G1 arrest [(Sherr and Roberts, 1995) and references therein]. In any case, both models are consistent with a multi-step activation pathway operating in G1 phase that prepares G1 nuclei to initiate S phase only in very late G1.

C.5 Both cyclin A/Cdk2 and cyclin E/Cdk2 are required to initiate optimally S phase in G1 nuclei Recombinant human cyclin A/Cdk2 and cylin E/Cdk2 triggered initiation of DNA replication in vitro synergistically up to a maximal efficiency of 35% (FIG. 7). Identical efficiencies were obtained with nuclear extract from S phase cells (FIGS. 4 and 5). A combination of both cyclins and nuclear extract did not increase the efficiency of initiation in vitro (data not shown). It is therefore very likely that the nuclear extract activated the same pathway as the cyclin-Cdk2 complexes to trigger initiation of DNA synthesis in G1 phase nuclei. The S phase nuclear extract had histone H1 kinase activity and contained cyclin A and Cdk2 proteins, but lower amounts of cyclin E than cyclin A as measured by immunoblotting (data not shown).

Our data strongly support a role of cyclins A and E completed to Cdk2 in the G1-to-S transition in the cell cycle. Overexpression of ectopic cyclin A, E (and D) genes in untransformed diploid rodent fibroblasts resulted in a shortening of the G1 phase and an accelerated entry into S in vivo (Ohtsubo and Roberts, 1993; Resnitzky et al., 1994; Wimmel et al., 1994; Resnitzky et al., 1995). Injection of anti-cyclin A or E antibodies, or of corresponding antisense RNA constructs, into mammalian cells inhibited the onset of S phase (Girard et al., 1991; Pagano et al., 1992; Zindy et al., 1992; Ohtsubo et al., 1995). The data reported in this paper demonstrate that cyclin A/Cdk2 and E/Cdk2 act synergistically to trigger S phase in vitro, and each cyclin/Cdk2 alone led to a significantly lower level of initiation. The two cyclin/Cdk-complexes therefore appear to act through two separate pathways that either converge in late G1, or act in succession, with active E-Cdk2 preceding A-Cdk2 to trigger the G1 to S transition. This latter possibility is supported by in vivo expression data, as the expression of cyclin E precedes cyclin A in the cell cycle (Girard et al., 1991; Pines and Hunter, 1991; Koff et al., 1992; Rosenblatt et al., 1992; Zindy et al., 1992; Henglein et al., 1994; Ohtsubo et al., 1995). The mitotic cyclin B1/Cdc2-complex on the other hand behaves differently. It is not only unnecessary for the G1-to-S transition in this system (FIG. 7), but inhibitory for initiation in vitro (data not shown). This is consistent with the known role of this cyclin in the regulation of mitosis (Nurse, 1990; Nurse, 1994). Unexpectedly, high concentrations of both cyclins A/Cdk2 and E/Cdk2 together dramatically inhibited the initiation of DNA replication in vitro (FIG. 7). The reason for this is unknown.

Table 1. DNA synthesis during a 2 h incubation in vitro.

G1 phase (6.5 h post mitosis) and S phase nuclei were incubated in a cytosolic extract and, where indicated, also in a nuclear extract from S phase cells in the presence of $\alpha P^{32}$-dATP for 2 h. The amount of synthesised DNA was determined by TCA precipitation. The percentage of nuclei undergoing DNA synthesis in each reaction was determined by incorporation of biotin-dUTP and fluorescence microscopy in parallel. G1 phase nuclei synthesising DNA in the absence of an S phase nuclear extract in reaction (b) were already shown to be S phase contaminants by prelabelling in vivo (see FIG. 1). Mean values of four independent experiments are shown.

REFERENCES

Belyaev, A. S., and Roy, P. (1993). *Nucl. Acids Res.* 21, 1219–1223.
Blow, J. J., and Laskey, R. A. (1986). *Cell* 47, 577–587.
Bradford, M. M. (1976). *Anal. Biochem.* 72, 248–254.
Cardoso, et al., (1993). *Cell* 74, 979–992.
Challberg, M. D., and Kelly, T. J. (1989). *Ann. Rev. Biochem.* 58, 671–717.
D'Urso, et al., (1990). *Science* 250, 786–791.
de Terra, N. (1967). *Proc. Natl. Acad. Sci. USA* 57, 607–614.
Desai, et al., (1992). *Mol. Biol. Cell* 3, 571–582.
Draetta, G. F. (1994). *Curr. Op. Cell Biol.* 6, 842–846.
Dulic, et al., (1992). *Science* 257, 1958–1961.
Girard, et al., (1991). *Cell* 67, 1169–1179.
Graham, et al., (1966). *Dev. Biol.* 14, 349–381.
Guttes, S., and Guttes, E. (1968). *J. Cell Biol.* 37, 761–772.
Harris, et al., (1966). *J. Cell Sci.* 1, 1–30.
Hartwell, L. H. (1974). *Bacter. Rev.* 38, 164–198.
Heichman, K. A., and Roberts, J. M. (1994). *Cell* 79, 557–562.
Heintz, N. H., and Stillman, B. W. (1988). *Mol. Cell Biol.* 8, 1923–1931.
Henglein, et al., (1994). *Proc. Natl. Acad. Sci. USA* 91, 5490–5494.
Hutchison, et al., (1987). *EMBO J.* 6, 2003–2010.
Jackman, et al., (1995). *EMBO J.* 14, 1646–1654.
Johnson, et al., (1993). The synchronization of mammalian cells. In *The cell cycle. A practical approach.*, P. Fantes and R. Brooks, eds. (Oxford: IRL press at Oxford University press), pp. 1–24.
Johnson, R. T., and Harris, H. (1969) *J. Cell Sci.* 5, 625–643.
Johnson, R. T., and Mullinger, A. M. (1975). *J. Cell Sci.* 18, 455–490.

Murray, A. W., and Kirschner, M. W. (1989). *Nature* 339, 275–280.
Nakamura, et al., (1984). *Exp. Cell Res.* 151, 123–133.
Nakayasu, H., and Berezney, R. (1989). *J. Cell Biol.* 108, 1–11.
Nasmyth, K. (1993). *Curr. Op. Cell Biol.* 5, 166–179.
Newport, J. (1987). *Cell* 48, 205–217.
Nugroho, T. T., and Mendenhall, M. D. (1994). *Mol. Cell Biol.* 14, 3320–3328.
Nurse, P. (1994). *Cell* 79, 547–550.
Nurse, P. (1990). *Nature* 344, 503–508.
Ohtsubo, M., and Roberts, J. M. (1993). *Science* 259, 1908–1912.
Ohtsubo, et al., (1995). *Mol. Cell Biol.* 15, 2612–2624.
Ord, M. J. (1969). *Nature* 221, 964–966.
Pagano, et al., (1992). *EMBO J.* 11, 961–971.
Pines, J., and Hunter, T. (1990). *Nature* 346, 389–401.
Pines, J., and Hunter, T. (1991). *J. Cell Biol.* 115, 1–17.
Pines, J., and Hunter, T. (1989). *Cell* 58, 833–846.
Rao, P. N., and Johnson, R. T. (1970). *Nature* 225, 159–164.
Resnitzky, et al., (1994). *Mol. Cell Biol.* 14, 1669–1679.
Resnitzky, et al., (1995). *Mol. Cell Biol.* 15, 4347–4352.
Resnitzky, D., and Reed, S. I. (1995). *Mol. Cell Biol.* 15, 3463–3469.
Romanowski, P., and Madine, M. A. (1996). *Trends Cell Biol.* 6, 184–188.
Rosenblatt, et al., (1992). *Proc. Natl. Acad. Sci. USA* 89, 2824–2828.
Sambrook, et al., (1989). *Molecular cloning. A laboratory manual.*, Second edition Edition (Cold Spring Harbor, N.Y., USA.: Cold Spring Harbor Laboratory Press.).
Schwob, et al., (1994). *Cell* 79, 233–24.
Sherr, C. H. (1994). *Cell* 79, 551–555.
Sherr, C. H., and Roberts, J. M. (1995). *Genes Dev.* 9, 1149–1163.
Shimamura, et al., (1988). *Mol. Cell Biol.* 8, 4257–4269.
Stillman, B. W. (1989). *Ann. Rev. Cell Biol.* 5, 197–245.
Tsai, et al., (1991). *Nature* 353, 174–177.
Wimmel, et al., (1994). *Oncogene* 9, 995–997.
Zetterberg, et al., (1995). *Op. Cell Biol.* 7, 835–842.
Zindy, et al., (1992). *Biochem. Biophys. Res. Comm.* 182, 1144–1154.

TABLE 1

DNA synthesis during a 2 h incubation in vitro

|   |   | pmole dNMP incorporated $10^5$ nuclei | % of nuclei replicating | pmole dNMP incorporated $10^5$ replicating nuclei |   |
|---|---|---|---|---|---|
| (a) | "S phase nuclei" | 182 | 95.0 | 191 |   |
| (b) | "G1 phase nuclei" | 9* | 8.2* | 134* | S phase contaminants |
| (c) | "G1 nuclei" + S nuclear extract | 32 | 19.3 | 167 | including S phase contam. |
| (d) | true G1 nuclei + S nuclear extract | 23 | 10.9 | 211 | excluding S phase contam. [(c) − (b)] |

*shown to be S phase contaminants by prelabelling in vivo (see FIG. 1)

Koff, et al., (1991) *Cell*, 66, 1217–1228.
Koff, et al., (1992). *Science* 257, 1689–1693.
Krude, T. (1995). *Exp. Cell Res.* 220, 304–311.
Krude, et al., (1996). *J. Cell Sci.* 109, 309–318.
Lee, M. G., and Nurse, P. (1987). *Nature* 327, 31–35.
Leno, et al., (1992). *Cell* 69, 151–158.
Li, J., and Kelly, T. (1984). *Proc. Natl. Acad. Sci. USA* 81, 6973–6977.
Lohka, M. J., and Masui, Y. (1983). *Science* 220, 719–721.
Manders, et al., (1992). *J. Cell Sci.* 103, 857–862.

What is claimed is:

1. A cell-free system comprising:

G1 phase nuclei, which are co-incubated in the presence of S phase cytosol or a fraction thereof and S phase nuclei, said system providing for the initiation of DNA replication under cell cycle control.

2. A cell-free system according to claim 1 wherein cyclin A and cyclin E both complexed to Cdk2 are separately added to the system.

3. A cell-free system according to claim 1 wherein the S phase cytosol or fraction thereof is supplemented with nucleoside and deoxynucleoside triphosphates.

4. A cell-free system according to claim 3 wherein a labelled deoxynucleoside triphosphate is included.

5. An assay method for a substance with ability to modulate DNA synthesis, the method comprising:
   (a) treating a cell-free system according to claim 1 with a test substance; and
   (b) determining DNA synthesis.

6. A method comprising, following identifying a substance as having ability to modulate DNA synthesis in accordance with claim 5, modifying the substance.

7. A method according to claim 6 wherein the substance is modified to alter a property of the substance.

8. A method according to claim 7 wherein the substance is modified to alter its ability to modulate DNA synthesis.

9. A method comprising, following identifying a substance as having ability to modulate DNA synthesis in accordance with claim 5, formulating the substance or a modified form thereof into a composition including at least one additional component.

10. A method according to claim 9 wherein the composition includes a pharmaceutically acceptable excipient.

11. A method according to claim 5, wherein the substance is an inhibitor of DNA synthesis.

12. A method according to claim 5, wherein the substance is a stimulator of DNA synthesis.

13. A cell-free system according to claim 1, wherein at least one component selected from the group consisting of cyclin A complexed to its cognate cyclin dependent kinase (Cdk2) and cyclin E complexed to its cognate cyclin dependent kinase (Cdk2), is separately added to the system.

14. A cell-free system comprising:
   G1 phase nuclei, which are co-incubated in the presence of S phase cytosol or a fraction thereof and wherein at least one component selected from the group consisting of cyclin A complexed to its cognate cyclin dependent kinase (Cdk2) and cyclin E complexed to its cognate cyclin dependent kinase (Cdk2) is separately added to the system, said system providing for the initiation of DNA replication under cell cycle control.

15. A cell-free system according to claim 14 wherein the S phase cytosol or fraction thereof is supplemented with nucleoside and deoxynuleoside triphosphates.

16. An assay method for a substance with ability to modulate DNA synthesis, the method comprising:
   (a) treating a cell-free system according to claim 14 with a test substance; and
   (b) determining DNA synthesis.

* * * * *